US010197545B2

(12) United States Patent
Sreekumar et al.

(10) Patent No.: US 10,197,545 B2
(45) Date of Patent: Feb. 5, 2019

(54) METHOD AND APPARATUS FOR MEASUREMENT OF A MATERIAL IN A LIQUID THROUGH ABSORPTION OF LIGHT

(71) Applicant: Advancedf Sensors Limited, Carrickfergus (GB)

(72) Inventors: Jeyan Sreekumar, Newtownabby (GB); Karl McBride, Gleno (GB); Neal McGeown, Crumlin (GB)

(73) Assignee: ADVANCED SENSORS LIMITED, Carrickfergus (GB)

( * ) Notice: Subject to any disclaimer, the term of this patent is extended or adjusted under 35 U.S.C. 154(b) by 122 days.

(21) Appl. No.: 15/340,536

(22) Filed: Nov. 1, 2016

(65) Prior Publication Data

US 2017/0115225 A1 Apr. 27, 2017

Related U.S. Application Data

(63) Continuation-in-part of application No. 14/812,026, filed on Jul. 29, 2015.

(51) Int. Cl.
*G01N 33/28* (2006.01)
*G01N 21/27* (2006.01)
(Continued)

(52) U.S. Cl.
CPC ........... *G01N 33/28* (2013.01); *G01N 21/274* (2013.01); *G01N 21/643* (2013.01); *G01N 21/645* (2013.01); *G01N 33/1833* (2013.01); *G01N 21/05* (2013.01); *G01N 2021/154* (2013.01); *G01N 2021/6423* (2013.01);
(Continued)

(58) Field of Classification Search
CPC .. G01N 21/645; G01N 21/64; G01N 21/8507; G01N 33/1833; G01N 33/2823; G01N 2021/648; G01N 21/05; G01N 21/274; G01N 21/643; G01N 33/28; G01N 2021/154; G01N 2021/6423;
(Continued)

(56) References Cited

U.S. PATENT DOCUMENTS 3,736,431 A 5/1973 Childs
3,936,190 A * 2/1976 Ohnishi ............... G01J 3/4406
250/458.1

(Continued)

OTHER PUBLICATIONS

O'Haver, T., "Comparison of Calibration Curve Fitting Methods in Absorption Spectroscopy", Nov. 24, 2010, Internet Archive Wayback Machine, https://web.archive.org/web/20101124184105/http://terpconnect.umd.edu:80/~toh/models/BeersLawCurveFit.html.*

*Primary Examiner* — David Porta
*Assistant Examiner* — Blake Riddick
(74) *Attorney, Agent, or Firm* — Snyder, Clark, Lesch & Chung, LLP

(57) ABSTRACT

The method and apparatus as shown in the present invention is to measure the absorption of light by material contained in a liquid. A transmitted signal is sent through a measurement window to a measurement chamber to a target point just inside the measurement window. The reflected signal indicates the amount of light absorbed by a material in the measurement chamber which allows for the amount of materials in a liquid to be determined. Adjustments are made through an optical block and a light control molecule to correct for variations in light intensity.

7 Claims, 15 Drawing Sheets

(51) Int. Cl.
*G01N 21/64* (2006.01)
*G01N 33/18* (2006.01)
*G01N 21/05* (2006.01)
*G01N 21/15* (2006.01)
*G01N 21/85* (2006.01)

(52) U.S. Cl.
CPC .............. *G01N 2021/6463* (2013.01); *G01N 2021/8528* (2013.01); *G01N 2201/0846* (2013.01)

(58) Field of Classification Search
CPC ... G01N 2021/6463; G01N 2021/6484; G01N 2021/8528; G01N 2201/0846
USPC ......... 250/458.1, 461.1, 269.1, 301, 574, 57
See application file for complete search history.

(56) References Cited

U.S. PATENT DOCUMENTS

| | | | |
|---|---|---|---|
| 3,999,863 A | 12/1976 | Schoneman | |
| 4,198,567 A * | 4/1980 | Eneroth | G01N 21/6408 250/459.1 |
| 4,622,468 A | 11/1986 | Stefanski et al. | |
| 4,981,362 A | 1/1991 | deJong et al. | |
| 5,166,747 A * | 11/1992 | Schroeder | E21B 47/102 250/256 |
| 5,185,645 A * | 2/1993 | Sartorius | G01B 11/0625 356/432 |
| 5,325,171 A | 6/1994 | Shimizu | |
| 5,446,280 A | 8/1995 | Wang et al. | |
| 5,617,205 A | 4/1997 | Dou et al. | |
| 5,751,417 A * | 5/1998 | Uhl | G01J 3/02 250/458.1 |
| 6,002,990 A | 12/1999 | Hanna | |
| 6,351,306 B1 | 2/2002 | Tedesco et al. | |
| 6,355,934 B1 * | 3/2002 | Osgood | G01N 21/6452 250/216 |
| 6,466,316 B2 | 10/2002 | Modlin et al. | |
| 6,485,300 B1 * | 11/2002 | Muller | A46B 15/0002 433/29 |
| 6,583,424 B2 | 6/2003 | Staton et al. | |
| 6,723,554 B1 | 4/2004 | Gaillon et al. | |
| 6,740,871 B1 | 5/2004 | Staton et al. | |
| 6,956,203 B2 | 10/2005 | Staton et al. | |
| 7,170,597 B1 * | 1/2007 | Hooper | G01N 21/6452 250/458.1 |
| 7,365,328 B2 | 4/2008 | Busch et al. | |
| 7,935,938 B2 | 5/2011 | Thabeth et al. | |
| 8,334,522 B2 | 12/2012 | Egger | |
| 8,804,115 B2 | 8/2014 | Yu et al. | |
| 2005/0239159 A1 * | 10/2005 | Freund | A01N 43/90 435/21 |
| 2007/0153279 A1 * | 7/2007 | Aasmul | G01J 1/04 356/417 |
| 2007/0291255 A1 * | 12/2007 | Larsen | G01J 3/02 356/73 |
| 2008/0123712 A1 * | 5/2008 | Zhou | G01N 21/39 372/55 |
| 2008/0204551 A1 * | 8/2008 | O'Connell | G02B 21/0008 348/79 |
| 2008/0291397 A1 * | 11/2008 | Tesar | A61B 3/12 351/221 |
| 2009/0032733 A1 * | 2/2009 | Thabeth | G01N 21/15 250/458.1 |
| 2012/0061589 A1 | 3/2012 | Thabeth et al. | |
| 2012/0162614 A1 * | 6/2012 | Kobayashi | G03B 21/204 353/31 |
| 2012/0228519 A1 * | 9/2012 | Gilmore | G01N 21/645 250/459.1 |
| 2012/0255361 A1 | 10/2012 | Thabeth et al. | |
| 2013/0038875 A1 * | 2/2013 | Schreiber | G02B 21/0032 356/364 |
| 2013/0100452 A1 | 4/2013 | Degner et al. | |
| 2013/0266797 A1 * | 10/2013 | Teramoto | C08L 33/12 428/327 |
| 2014/0133011 A1 * | 5/2014 | Schwedt | G02B 21/0032 359/298 |
| 2014/0234984 A1 * | 8/2014 | Juuti | G01N 21/33 436/172 |
| 2015/0260639 A1 | 9/2015 | Thabeth et al. | |
| 2015/0276589 A1 * | 10/2015 | Wagner | G01N 21/39 356/440 |
| 2016/0054275 A1 | 2/2016 | Andrews | |

\* cited by examiner

EXAMPLE 1

EXAMPLE 2

EXAMPLE 3

EXAMPLE 4

METHOD AND APPARATUS FOR MEASUREMENT OF A MATERIAL IN A LIQUID THROUGH ABSORPTION OF LIGHT

CROSS REFERENCE TO RELATED APPLICATIONS

This is an improvement over U.S. Pat. No. 7,935,938, issued on May 3, 2011, entitled "Apparatus for Measuring Fluorescent Material in a Liquid," which patent is hereby incorporated by reference, and a continuation-in-part of U.S. patent application Ser. No. 14/812,026, filed on Jul. 29, 2015.

BACKGROUND OF THE INVENTION

Technical Field

This invention relates to an apparatus for measuring fluorescent material in a liquid and, more particularly, to measuring material in a liquid through the absorption of light.

Description of the Prior Art

With the world's dependency on oil, more oil is being processed in oil refineries and shipped by pipelines than ever before. Many of the pipes (a) leading from/to oil production or (b) within refining operations require measuring the amount of oil that may be in a liquid (mainly water) flowing in the pipes. To aid in this process, in-line measuring apparatuses are commonly used to measure the amount of oil that is present in the pipe.

When subject to certain lights, oil has a natural fluorescence. The common way of determining the amount of oil presence is to measure the amount of fluorescence that can be processed. The measuring of the amount of oil present is commonly done by a fluorometer. A typical in-line fluorometer has an excitation light source which transmits the light onto the sample to a measurement region through a measurement window. When the oil in sample absorbs the light, it fluoresces. The resultant fluorescence light is transmitted back through the measurement window and is received by the fluorescence detector. By measuring the amount of fluorescent light, the amount of oil present in the water can be determined. However, in the prior systems, the measurement was accurate only up to a certain concentration of oil in water. The incorporated reference would only detect oil in water up to approximately 1,000 parts per million (hereinafter "ppm") before measurements started losing accuracy.

Applicant has discovered modifications that can be made to the incorporated reference to greatly improve the accuracy of measurements of oil-in-water in ppm at higher concentrations, which significantly increases accuracy of measurements from 1,000 ppm to 100,000 ppm (10%) of oil in water.

Further, Applicant has discovered that a very similar apparatus may be used to measure other materials in a liquid through an absorption of light technique. The absorption of light technique requires a light source plus continual adjustments to mitigate any inaccuracies of changes in the light source output.

BRIEF SUMMARY OF THE INVENTION

It is an object of the present invention to extend the range of measurements of the incorporated reference to higher ppm of oil in water.

It is another object of the present invention to modify the incorporated reference to use a single channel through which an excitation signal is transmitted and a fluorescent signal is received from a measurement chamber.

It is yet another object of the present invention to utilize an optical fiber for (1) transmitting the excitation signal and (2) receiving the fluorescent signal from the oil in water to determine in ppm a concentration of oil therein.

It is a further object of the present invention to modify the incorporated reference to use a laser as an excitation signal and spectrometer as a detector of the fluorescent signal.

It is yet another object of the present invention to modify the incorporated reference so that the target point for the fluorescent is close to the inner face of the measurement window.

It is yet another object of the present invention to modify the incorporated reference wherein the transmitted signal and the fluorescent signal are arranged such that the line of sight of the excitation signal and a fluorescent signal lie in a common plane which is not perpendicular with the inner surface of the measurement window.

It is still another object of the present invention wherein the line of sight of the excitation signal is at an obtuse angle with the line sight to the fluorescent signal.

It is another object of the present invention to have a measurement chamber with a measurement window with a single channel through which an excitation signal is transmitted and a fluorescent signal is detected using bifurcated fiber optics and an ultrasonic transducer for keeping the measurement window clean.

It is another object of the present invention to modify the incorporated reference so that lines of sight of (1) an excitation signal and (2) another light guide intersect in a measurement chamber to define a target region from which fluorescent light may be detected, said target region being located within the measurement chamber substantially at the inner face.

In the continuation-in-part application, it is another object of the present invention to provide a method and apparatus for measurement of material in a liquid through absorption of light.

In the continuation-in-part application, it is further object of the invention to provide a light source of a constant intensity.

In the continuation-in-part application, it is also an object of the present invention to mitigate any inaccuracies as a result of a change in intensity of the light output.

In the continuation-in-part application, it is yet another object of the present invention to provide a stable sample measurement, irrespective of variations in light source output.

The apparatus and method for measuring material in a liquid through use of an absorption technique is shown in the continuation-in-part application. The apparatus comprises a measurement chamber containing a liquid to be analyzed, a light source to transmit the light at a defined target region of the measurement chamber, the absorbed light from the target region being measured by a detector to determine the concentration of material within the measurement chamber, the angle between the transmitted light and the absorbed light being very small. The apparatus includes an optical block comprising beam splitters and an optical attenuator. A software module mitigates any inaccuracies as a result of a change in intensity of the light output from the emission source. The optical attenuator is adjusted to increase or decrease the light intensity to a level similar to that received from the target region. The software module controls light stability, which software module uses a mathematical model to compensate for deviations in sample measurements due to variations in optical system components and the environment. This results in a stable sample measurement, irrespective of light source output.

BRIEF DESCRIPTION OF THE DRAWINGS

FIG. 4(a) is measurements of fluorescent materials at different ppm in the incorporated reference of U.S. Pat. No. 7,935,938.

DESCRIPTION OF THE PREFERRED EMBODIMENT

Figure 1:
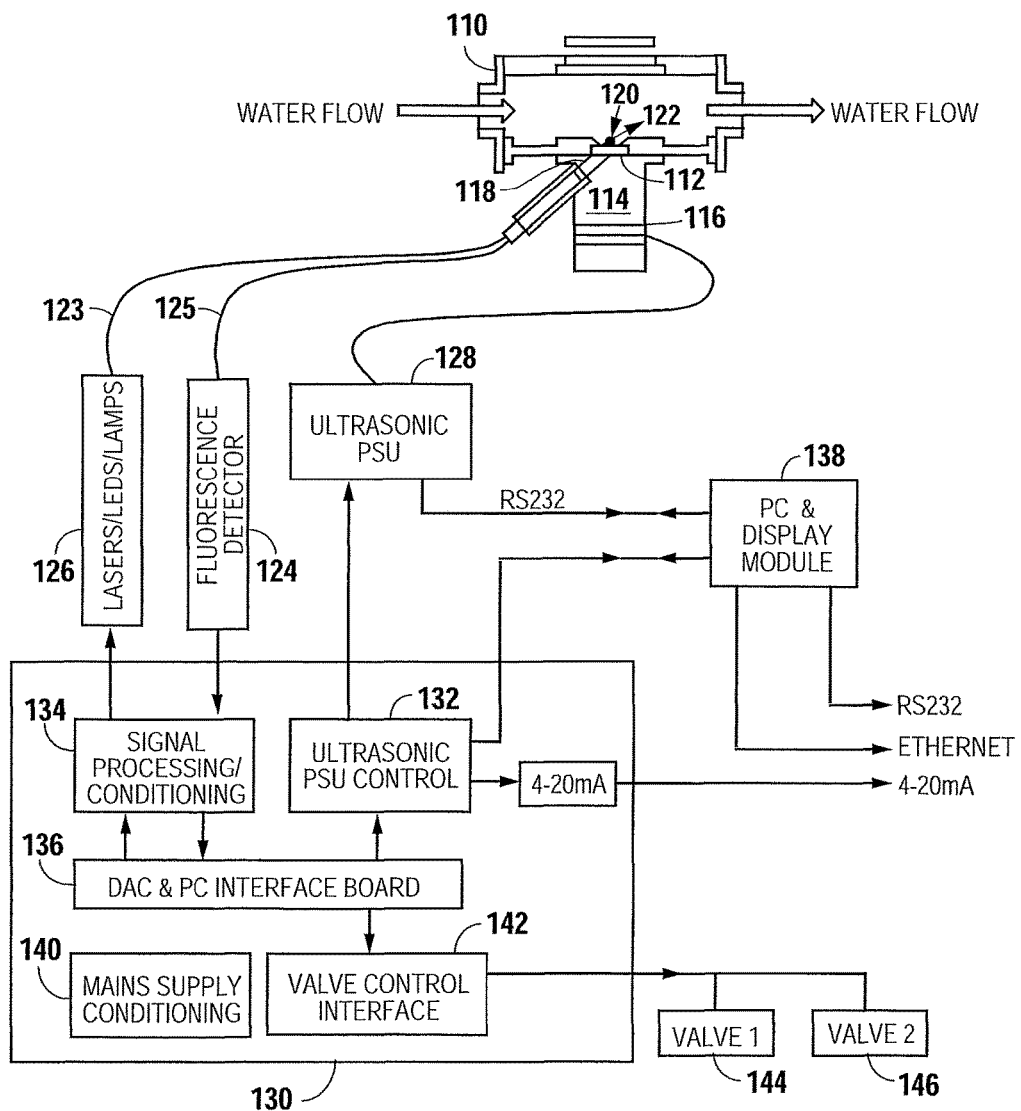
FIG. 1 is a schematic view of an apparatus embodying the present invention.

Having previously incorporated by reference U.S. Pat. No. 7,935,938, over which the present invention is an improvement, all reference numerals given herein below will start with the number 110 or higher so that none of the reference numerals will conflict with the reference numerals of the incorporated reference.

Referring to FIG. 1 of the present invention, a measurement chamber 110 is shown with water flowing there through. A measurement window 112 is provided on one side of the measurement chamber 110. In contact with the measurement window 112 is a coupling mass 114, with piezoelectric transducers 116 being located in the coupling mass 114 but away from the measurement window 112.

Connecting through the coupling mass 114 to the measurement window 112 is a single channel 118. Through the single channel 118, an excitation signal 122 is transmitted and fluorescent light 120 is collected or received using the light guides 123 and 125, respectively. The excitation signal 122 can be lasers, light emitting diodes or lamps 126. What is required is that the excitation signal 122 cause oil particles contained in the water flow to fluoresce so that the fluorescent light 120 can be detected by fluorescent detector 124. The excitation signal 122 is provided by an excitation source 126. The piezoelectric transducers 116 are energized by ultrasonic power supply 128.

The apparatus as shown in FIG. 1 has a master circuit board 130. While the composition and configuration of the circuitry may vary, an illustrated example of the circuitry includes an ultrasonic power supply control 132 for the ultrasonic power supply 128. A signal processing/conditioning unit 134 prepares a signal for the excitation source 126 (i.e., lasers/LEDs/lamps) and conditions the fluorescent light signal received from the fluorescent detector 124.

An interface unit 136 provides interfacing between the signal processing/conditioning unit 134, ultrasonic power supply control 132 and the computer 138. The computer 138 will have an internal display module, plus the computer 138 can either (1) connect to an RS232 connector or (2) to the Ethernet. The computer 138 will be appropriately programmed to operate the apparatus shown in FIG. 1. The computer 138 may be at the site with the rest of the apparatus shown in FIG. 1, or remotely located.

A power supply conditioning unit 140 is provided to operate the circuitry shown in FIG. 1.

Fluid flow through the measurement chamber 110 may be controlled by valve control interface 142, which controls operation of valve 144 or valve 146. Valve 144 may be located at one end of the measurement chamber 110, and valve 146 may be located at the opposite end thereof so that a liquid sample may be captured within measurement chamber 110 if desired.

Figure 2:
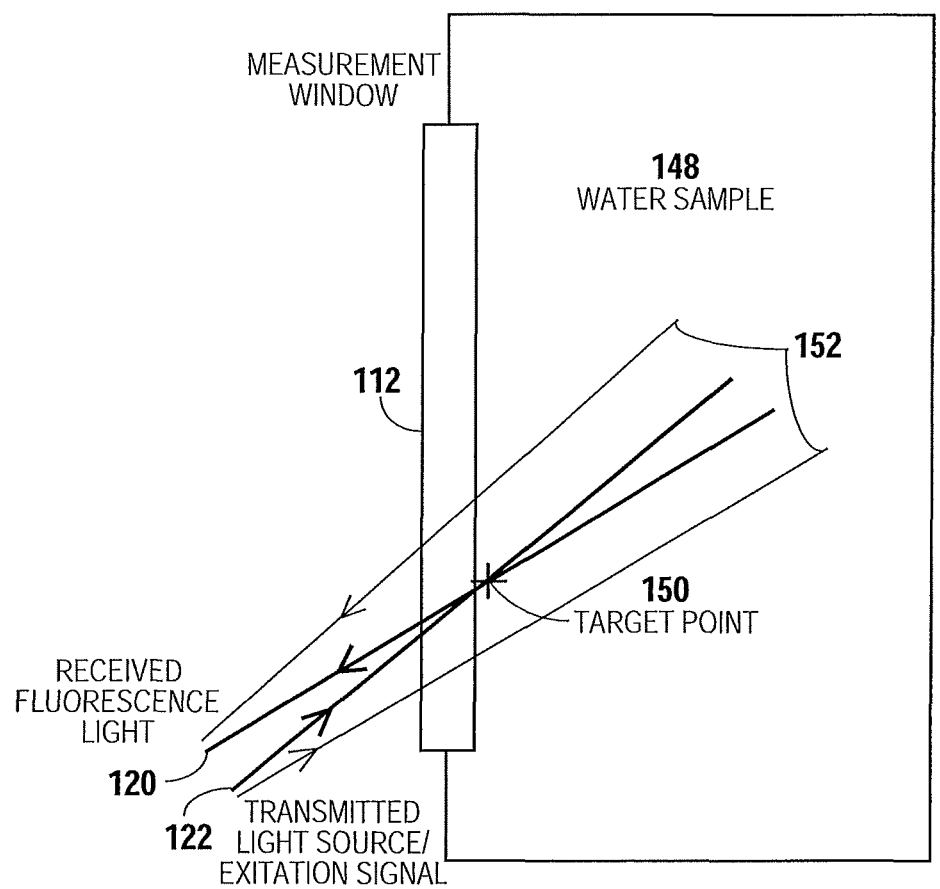
FIG. 2 is a pictorial view of a measurement chamber from the apparatus as shown in FIG. 1.

Referring now to FIG. 2, a water sample 148 is shown, which water sample 148 could be inside of measurement chamber 110. A measurement window 112 is provided through which access is obtained to the water sample 148. The excitation signal 122 is transmitted through the measurement window 112 to a target point 150, which target point 150 is just inside the measurement window 112. Any oil contained in the water sample 148 at target point 150 will create a fluorescent light 120 that is received back through the measurement window 112. As can be seen in FIG. 2, the angle between the excitation signal 122 and the fluorescent light 120 is very small. The excitation signal 122 and the fluorescent light 120 are very close together and are within a narrow envelope 152.

Figure 3:
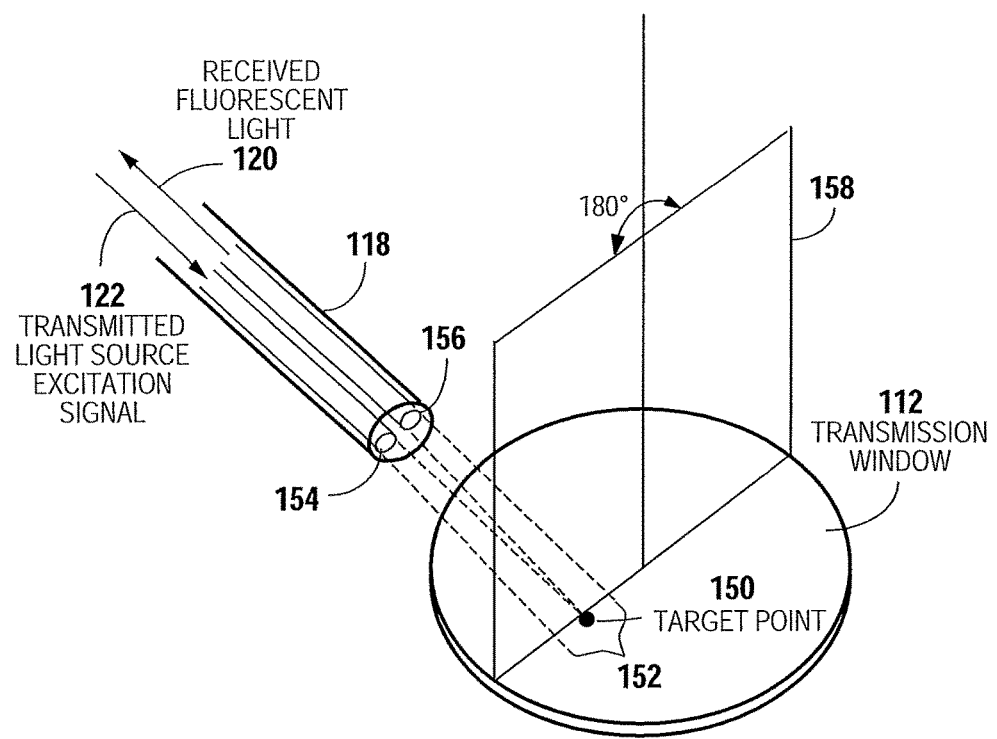
FIG. 3 is a schematic view of a preferred spatial relationship between a transmitted excitation light and a received fluorescent signal from the apparatus shown in FIG. 1.

Referring to FIG. 3, a further pictorial illustration of how the excitation signal 122 and the fluorescent light 120 are transmitted and received is illustrated. The single channel 118 (a) provides the excitation signal 122 and (b) receives the fluorescent light 120. Inside of the single channel 118 are fiber optic ends 154 and 156. The fiber optic ends 154 may be a single fiber optic that is split on the end thereof, are two separate strands of fiber optics contained in single channel 118. In either event, the fiber optic ends 154 and 156 are in close proximity to each other. The angle at which the excitation signal 122 strikes the transmission window 112 is at a substantial angle to the perpendicular plane 158 of the transmission window 112. Likewise, the angle at which the fluorescent light 120 is received from the target point 150 is also at a substantial angle with respect to the perpendicular plane 158.

Using the invention as shown in the incorporated reference, it is difficult to make measurements of oil-in-water for both conventional light and medium crude oils if the ppm's exceed the 1,000 ppm range. This is demonstrated in FIG. 4A attached hereto where measurements are made of a crude oil for parts per million (ppm) varying from 0 to 5,000. As can be seen in FIG. 4A if the ppms exceed 1,000, the relationship becomes non-linear and concentration quenching occurs between concentrations 1,000 ppm and 5,000 ppm. FIG. 4A gives the light intensity plotted versus the wavelength for a crude oil at varying ppms. The light intensity plotted versus ppm is shown in the upper right plot.

Figure 4B:
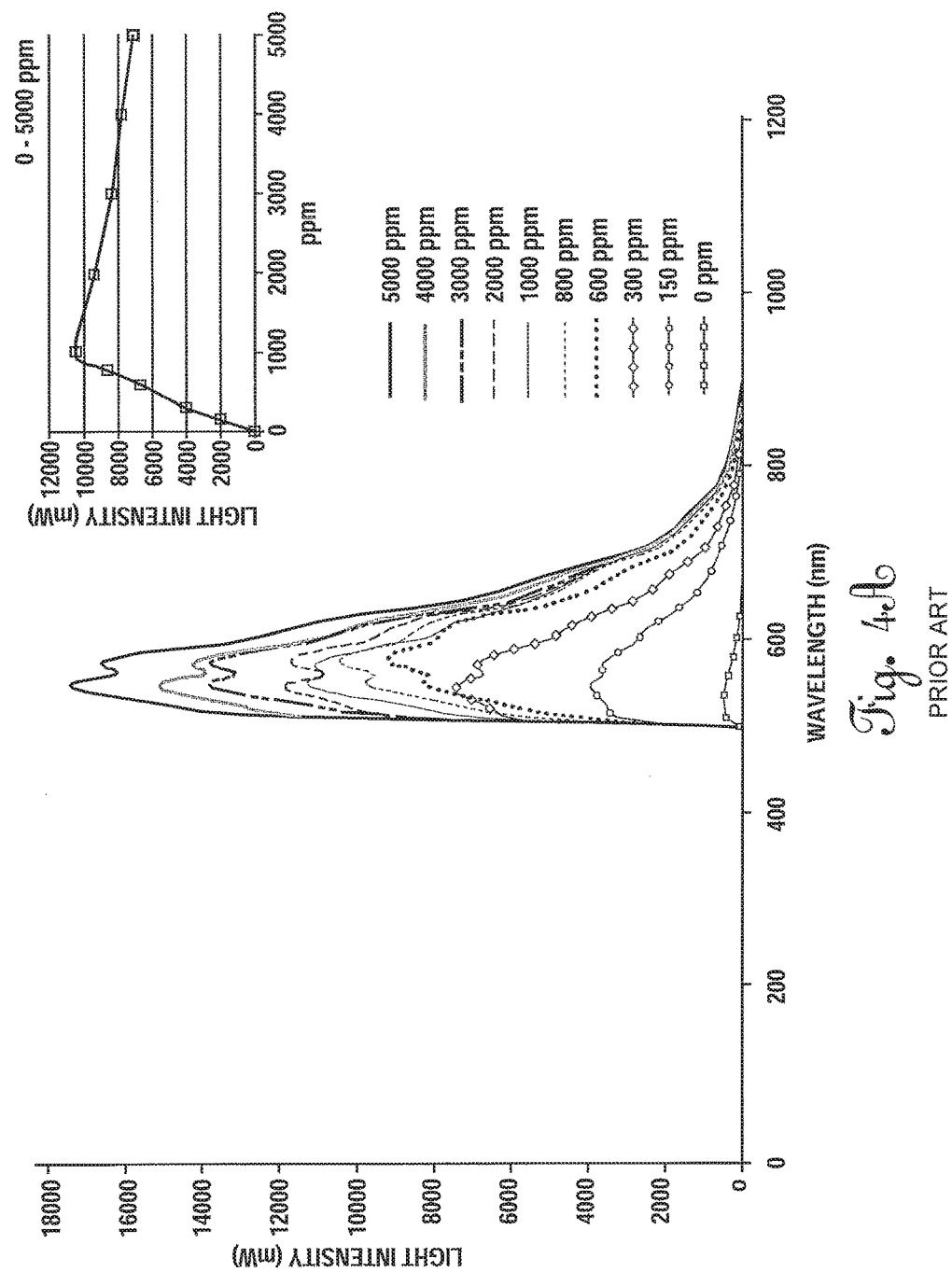
FIG. 4(b) is measurements of the fluorescent material at different ppm in a system incorporating the current improvements over the incorporated reference.
Figure 4B:
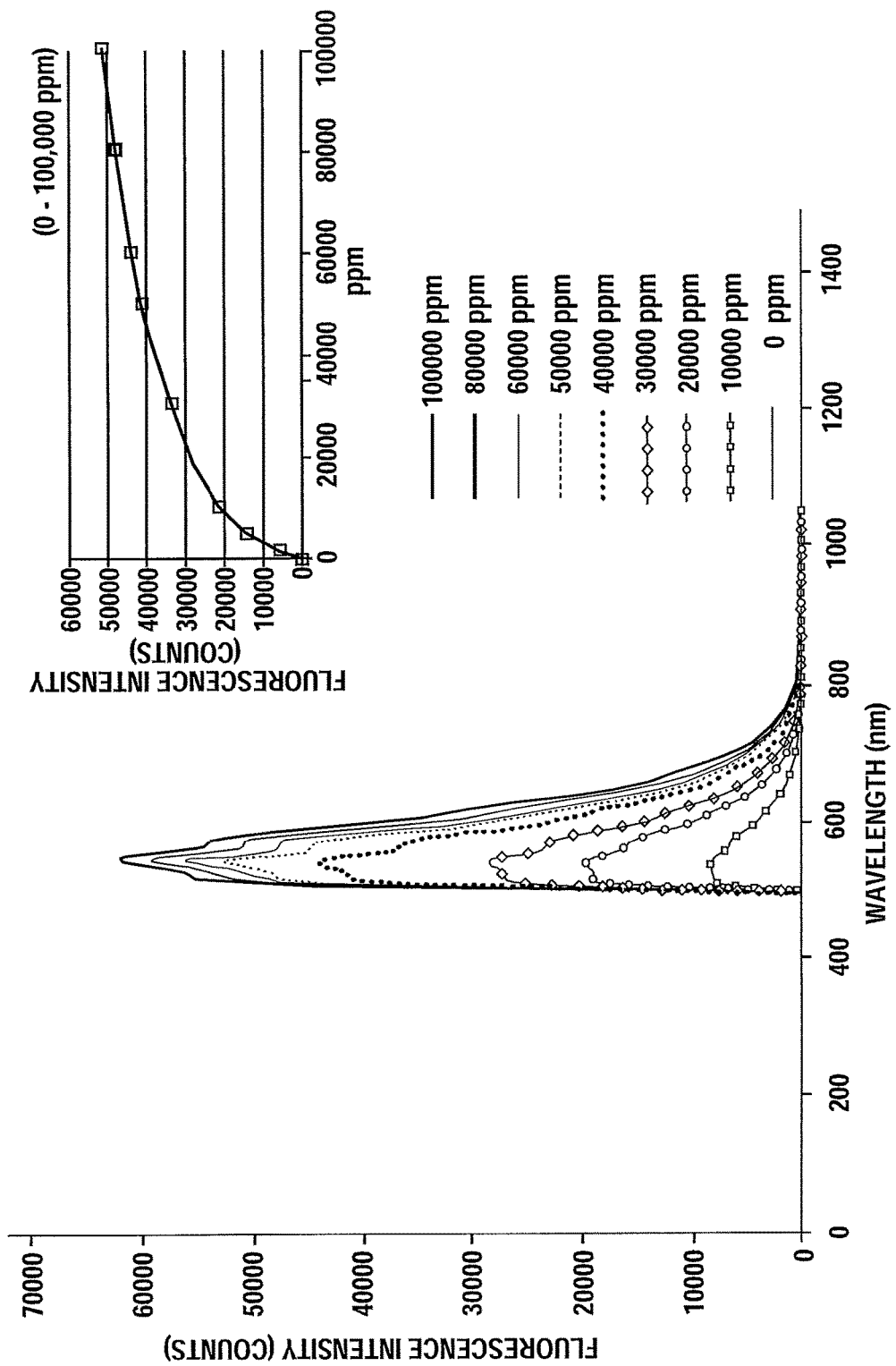

Modifying the prior invention incorporated by reference to utilize the features shown herein for crude oil is again run, but at higher ppm's range of 0 to 100,000 (see FIG. 4B). As can be seen in the upper right chart of FIG. 4B, the light intensity continues as a linear function of the ppms up to approximately 100,000 ppm. This illustrates how the incorporated invention once modified as illustrated herein increases the sensitivity of the incorporated reference at higher ppm' of light-to-medium weight crude oil.

Different oils were examined and the results obtained were similar to the discussed results.

Figure 5:
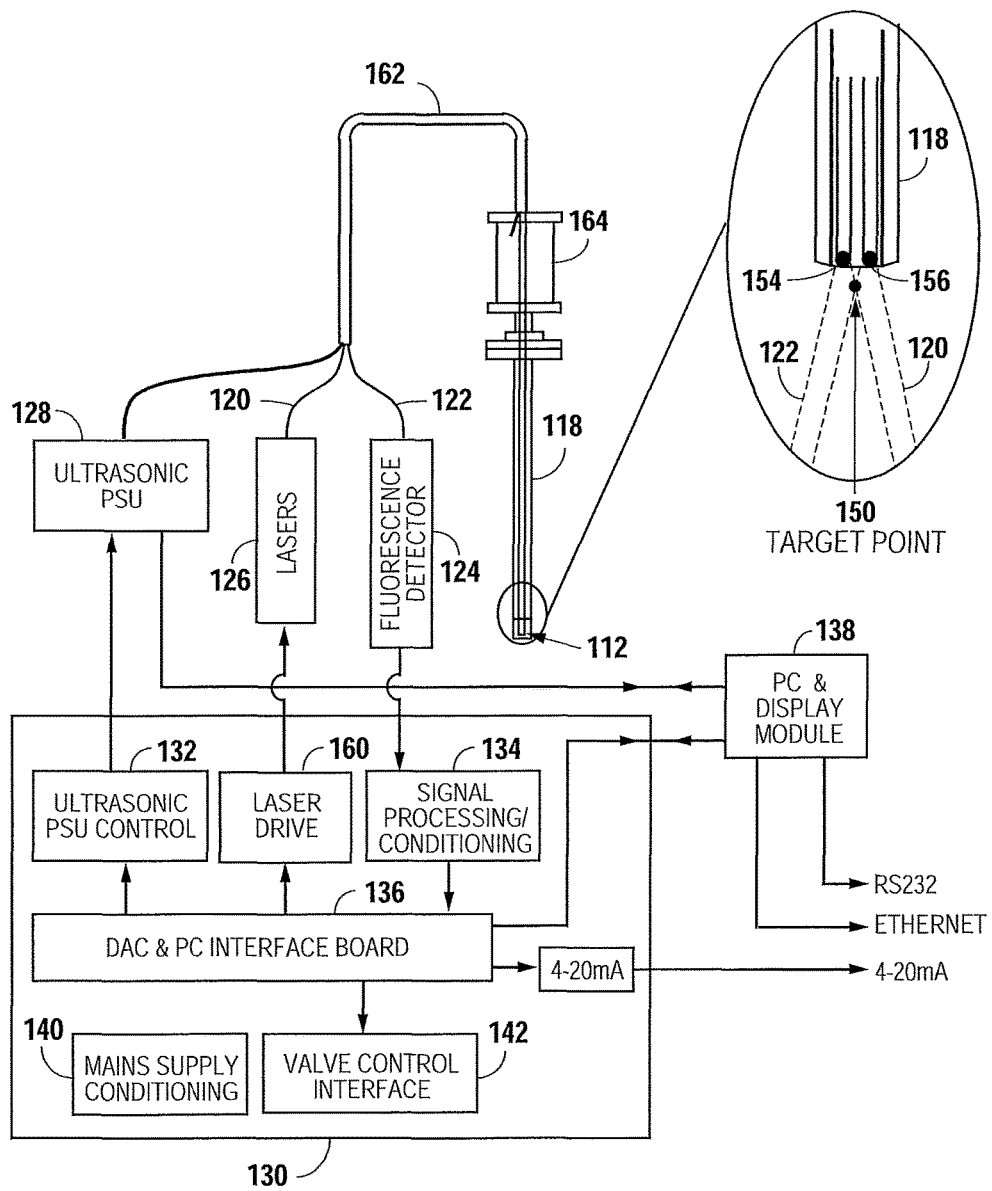
FIG. 5 is a modified schematic from FIG. 1 further illustrating changes from the incorporated reference.

Referring to FIG. 5, the apparatus as shown in FIG. 1 is given in further detail with the single channel 118 being illustrated in an enlarged view. In this embodiment as shown in FIG. 5, the excitation source 112 of lasers has a laser drive 160.

A single cable 162 connects to the ultrasonic transducer 164, which then has a single channel 118 pointing at the target point 150 through the measurement window 112. Inside of the single channel 118 are the fiber optic ends 154 and 156. The fiber optic ends 154 and 156 may be a single fiber optic split on each end thereof, or two separate fiber optic strands. In either event, fiber optic ends 154 and 156 are located adjacent to each other. Therefore, the angle between the excitation signal 122 and the fluorescent light 120 is very small; however, that angle is enlarged in FIG. 5 for purposes of illustration.

FIGS. 6-10 are added in the continuation-in-part patent application. To avoid confusion with U.S. Pat. No. 7,935,938 and U.S. patent application Ser. No. 14/812,026, filed on Jul. 19, 2015, the numerals applied to FIGS. 6 through 10 will start with the number 200 or higher.

Figure 6:
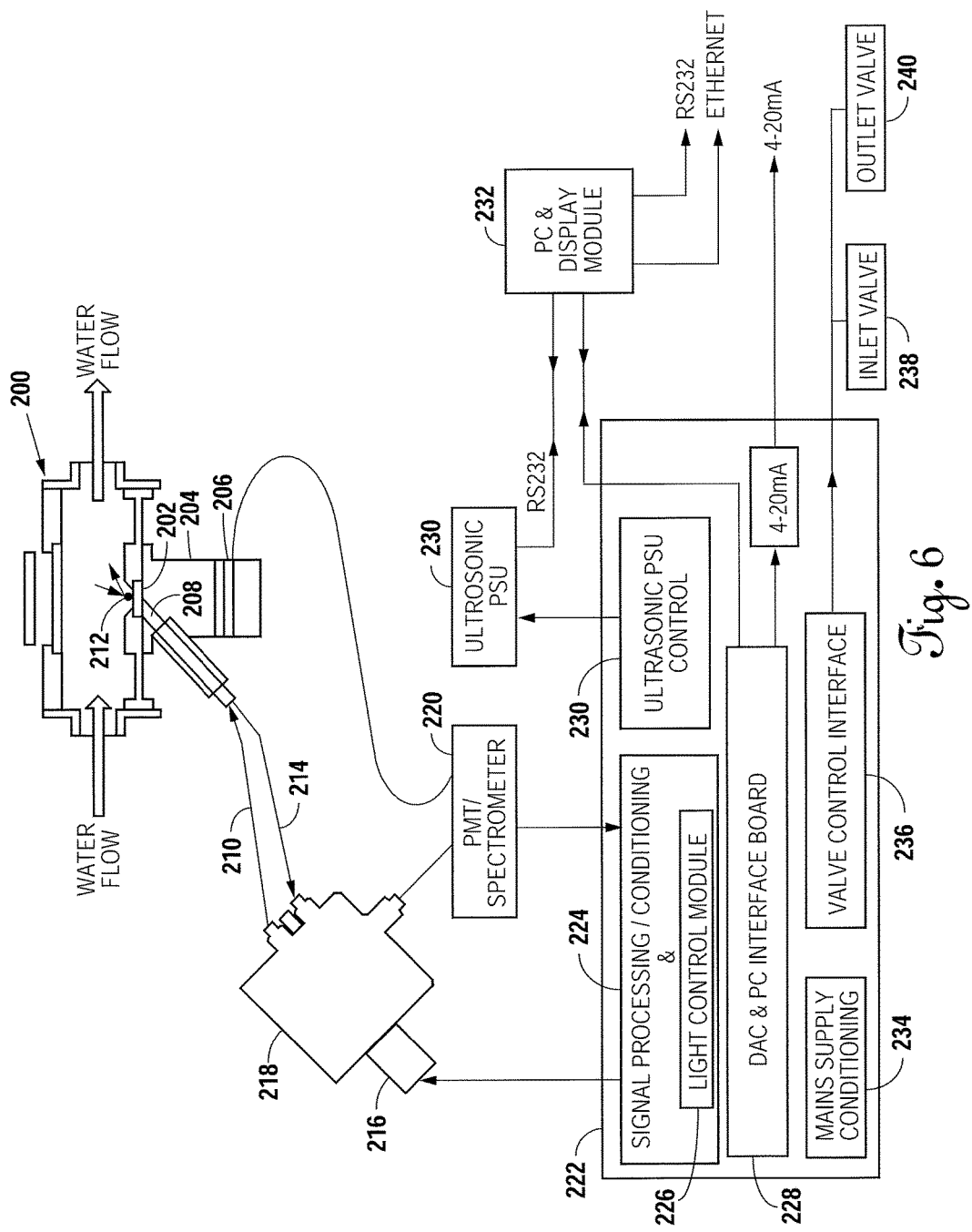
FIG. 6 is a schematic view of an apparatus for measurement of material in a liquid through absorption of light.

Referring to FIG. 6, a measurement chamber 200 is shown. Water flows through the measurement chamber 200 in the direction indicated by the arrows. The measurement chamber 200 has a measurement window 202 in one side thereof. Coupled to the measurement window 202 is a coupling mass 204 with piezoelectric transducers 206 located on one end of the coupling mass 204. A single channel 208 extends through coupling mass 204 to the measurement window 202. The single channel 208 has (a) a transmitting fiber optic end for delivering a transmitted signal 210 to a target point 212 and (b) a receiving fiber optic end adjacent thereto for receiving absorbed light 214 from target point 212.

A light source 216 transmits light through an optical block 218 to give a transmitted signal 210 through the single channel 208 to the target point 212. Part of the transmitted signal 210 (i.e., light) is absorbed by material at the target point 212. The absorbed light is reflected to give the amount of absorbed light 214.

The transmitted signal 210 is created by any suitable type of excitation light signal that can be generated by lasers, light emitting diodes or lamps as may be contained in the light source 216.

The transmitted signal 210 from the light source 216 is transmitted through the measurement window 202 onto the material in the liquid to be measured at target point 212. A part of a transmitted signal 210 is absorbed into some organic molecules present in the material at specific wavelengths and the absorbed light is detected. The transmitted signal 210 has a broader wavelength wherein the organic molecules are detected directly by measuring changes in absorption at a defined target point 212 using a detector such as PTM/Spectrometer 220 measuring at the absorption wavelengths. The target point 212 shown in FIG. 6 is close to the inside face of a measurement window 202 wherein the angle of measurement of the detector 220 is obtuse. The path link of the transmitted signal 210 and absorbed light 214 through the sample to the target point 212 is fixed.

A master control board 222 is provided in the invention illustrated in FIG. 6. The master control board 222 has signal processing/conditioning 224 which has as a subpart thereof a light control module 226. The light control module 226 is used to compensate for deviations in the transmitted signal 210, which are deviations in the light beam from the light source 216. The signal processing/conditioning unit 224 prepares a signal for the light source 216 and conditions the signal received by detector 220 from the absorbed light 214 via the signal channel 208 from the target point 212.

The DAC and PC interface board 228 provides interfacing between the signal processing conditioning unit 224, the ultrasonic power supply unit 230 and the PC and display module 232. The PC and display module 232 has an internal display module plus a computer that can either (1) connect to an RS 232 connector or (2) to the Ethernet. The computer within the PC and display module 232 will be appropriately programmed to operate the apparatus shown in FIG. 6. The PC and display module 232 may be on location at the site or remotely located.

A main supply conditioning 234 is used to condition power used to operate the master control board 222.

Flow through the measurement chamber 200 is controlled by valve control interface 236 which operates inlet valve 238 or outlet valve 240 to control flow through measurement chamber 200. By closing both the inlet valve 238 and the outlet valve 240, a liquid sample may be captured with the measurement chamber 200.

Figure 8:
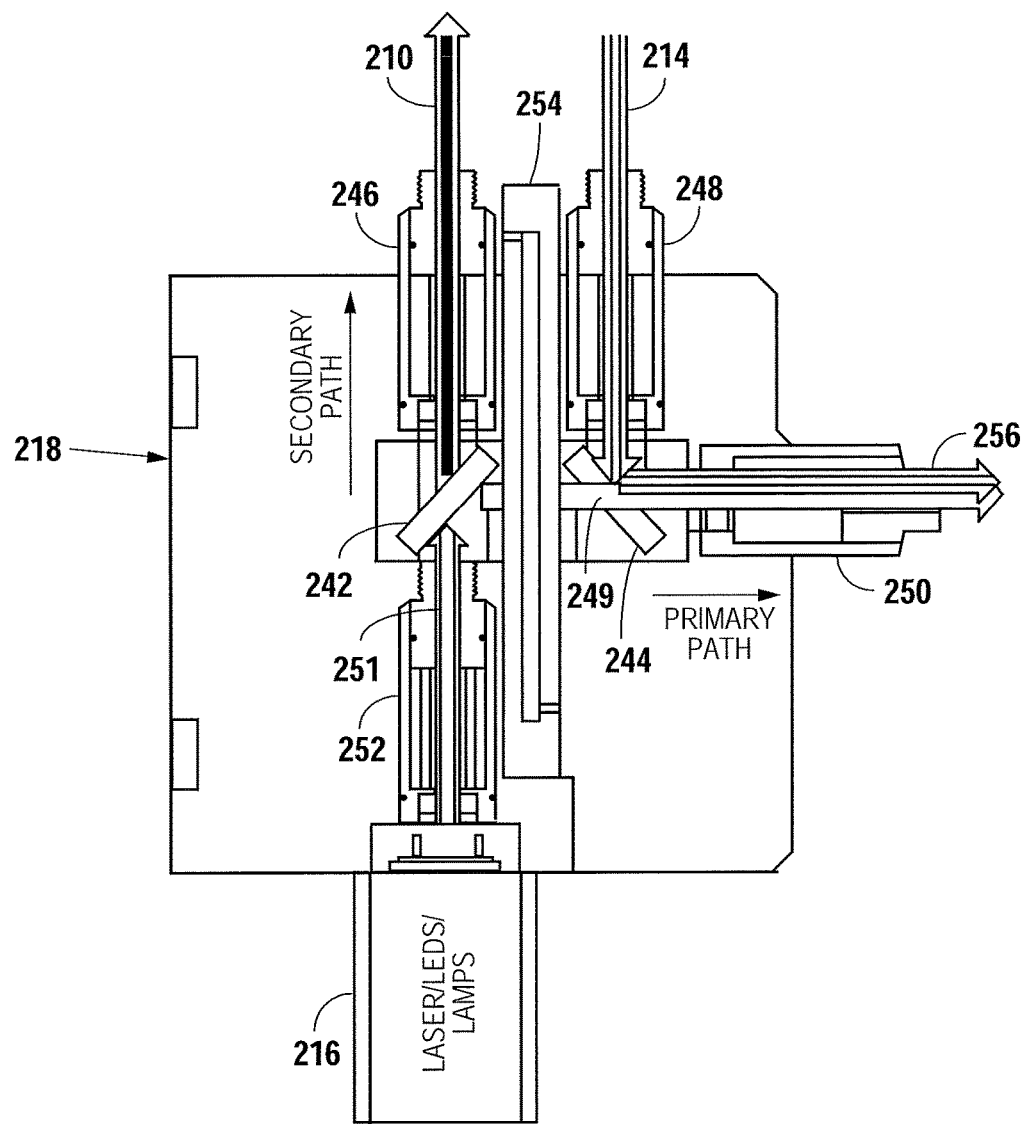
FIG. 8 is an enlarged pictorial view of the optical block shown in FIG. 6.

Referring now to FIGS. 6 and 8 in combination, the internal workings of the optical block 218 will be explained in more detail. Light 251 from the light source 216 travels through the beam splitters 242 and 244. Colminators 246, 248, 250 and 252 refocus the light into a beam.

The light source 216 provides light 251 through a colminator 252 to the beam splitter 242. From the beam splitter 242, a portion of the light flows through colminator 246 to provide the transmitted signal 210. The absorbed light 214 is received through colminator 248 before it hits beam splitter 244. Also transmitted through beam splitter 294 is light 249 that is reflected by beam splitter 242. Both light 249 and absorbed light 214 give recombined light beam 256 which travels through a colminator 250 to the detector 220 (PTM/Spectrometer).

Contained within the optical block 218 is a variable optical attenuator 254 to avoid saturation of detector (PMT/Spectrometer) 220.

Light 251 from the light source 216 is first colminated in colminator 252 and then sent through beam splitter 242 to divide into two beams. Beam splitter 242 is a long pass dichroic mirror which is highly reflective below the cut-off wavelength and highly transmissive above the cut-off wavelength, whereby the transmitted light is split at a cut-off wavelength such that wavelengths above the cut-off wavelength are transmitted into the measurement chamber 200, but wavelengths below the cut-off wavelength are reflective to the second beam splitter 244. The single channel 208 (see FIG. 6) is used both for the transmitted signal 210 and the absorbed light signal 214. The signal channel 208 is a bifurcated optical filter in a custom bifurcated assembly with blue silicone covered steel Monocoil with two optical legs. One leg is arranged to deliver the transmitted signal 210 from the light source 216 into the measurement chamber 200 and the other leg being arranged to carry absorbed light 214 from the measurement chamber 200 to the detector 220.

Figure 9:
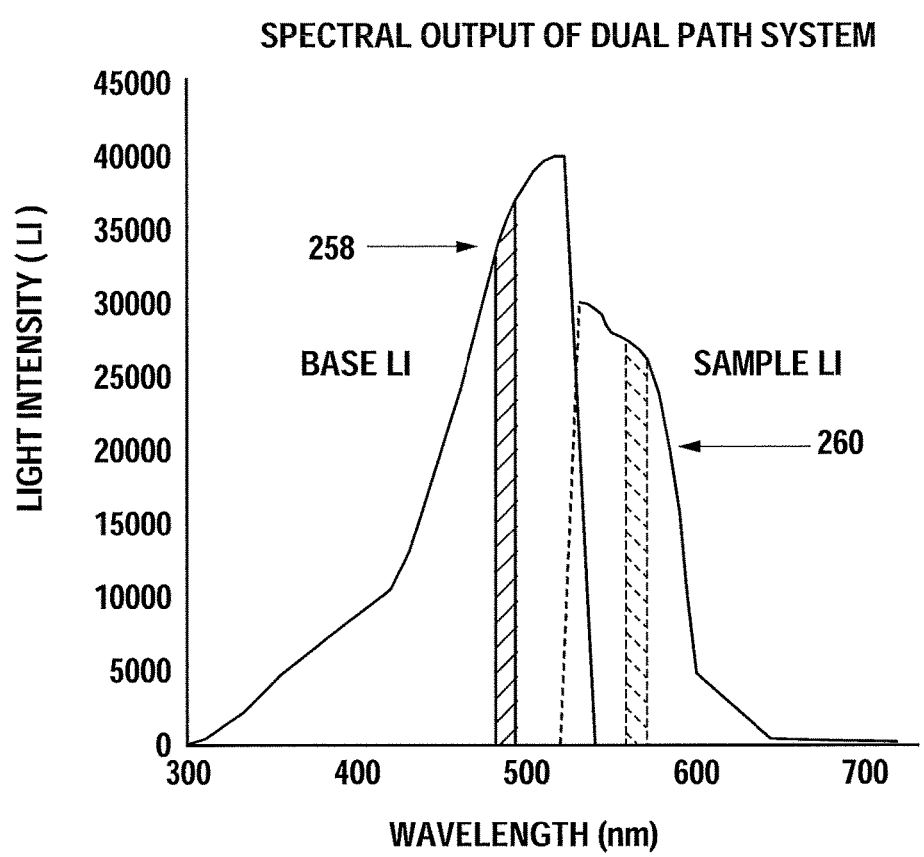
FIG. 9 is a graft of light intensity versus wavelength showing the spectral output of a dual path system.

The secondary beam splitter 244 as shown in FIG. 8 is a short pass dichroic mirror, which is highly reflective above the cut-off wavelength and highly transmissive below. The secondary beam splitter 244 is used to (1) reflect the absorbed light signal 214 being received from the measurement chamber 200 and (2) transmit there through the light 249 reflected by beam splitter 242 with the two light beams being recombined light beams 256 that are passed to the detector 220. Detector 220 upon receiving the recombined light beams 256 produces a single spectral output as shown in FIG. 9 with the part below the cut-off wavelength being area 258 and the part above the cut-off wavelength being area 260. Variable optical attenuator 254 within the optical block 218 attenuates the light of the recombined light beams 256 to avoid saturation of the detector 220.

The light control module 226 shown in FIG. 6 is programmed to control the deviation from a base light intensity as a result of a change in light output from the light source 216. The light control module 226 is used in conjunction with the optical block 218 to compensate for deviations in sample measurements due to variations in the optical system components and the environment on a real-time basis. This counteracts variations in output of the light source 216 while matching the principles of traditional absorption measurements. The net result is a stable sample measurement irrespective of the intensity of the light source 216.

Figure 10:
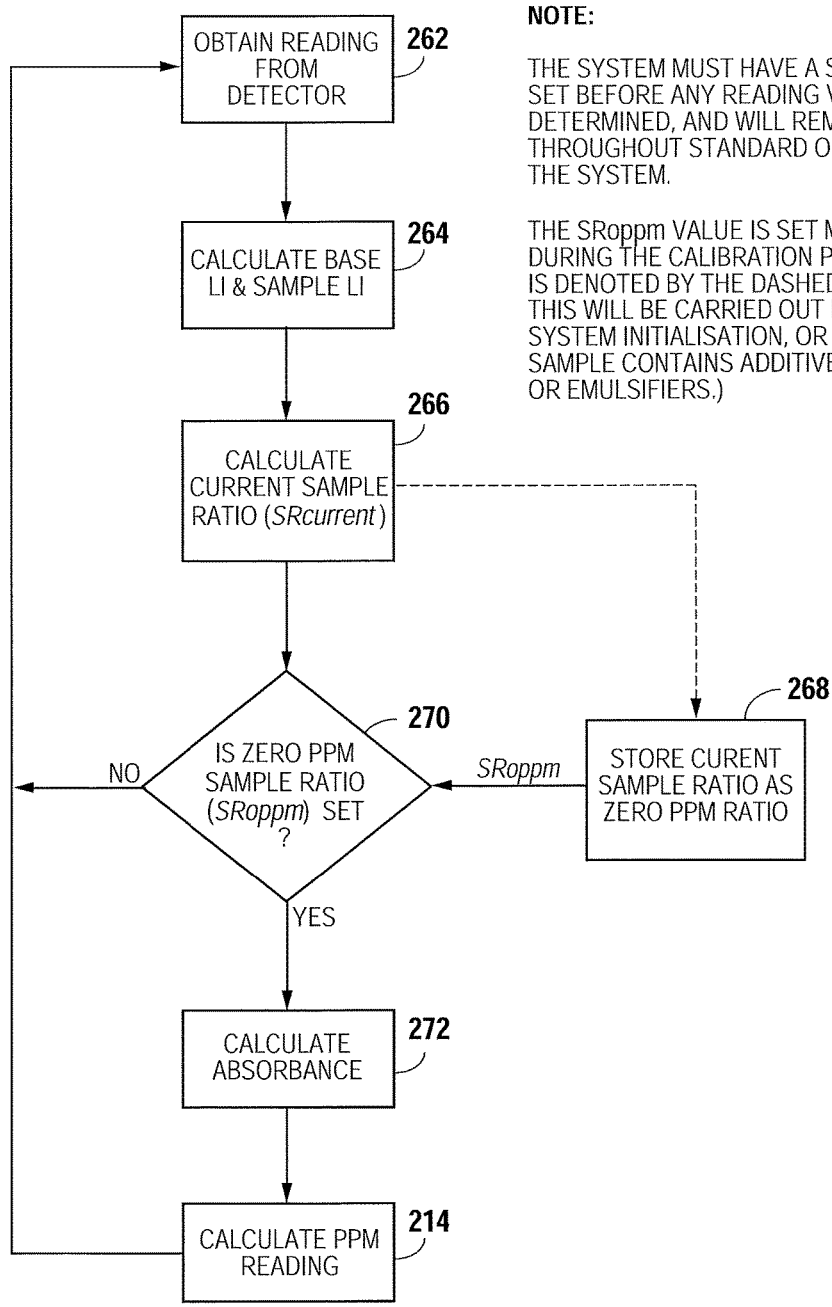
FIG. 10 is a flow chart illustrating the operational logic of the light control module in FIG. 6.

FIG. 10 shows a flow chart illustrating the operation of the light control module 226. The light control module 226 determines the value of a sample in a way that counteracts variants in the output of the light source 216.

During calibration, a water sample will be placed in the measurement chamber 200. A blank sample ratio ($SR_{OPPM}$) will be set equal to a current sample ratio ($SR_{current}$). From this point onward, the light control module will carry out the steps shown in FIG. 10.

Light is generated from the light source 216 at a cut-off wavelength to obtain an absorption response from a water sample within the target point 212 of the measurement chamber 200 to detect light intensities (LI) being received from the secondary and primary optical paths by means of detector 220 to generate a single spectral output as shown in FIG. 9 with two distinguishable areas for the water sample. This first step is to obtain a reading from the detector 262. The second step is to calculate base LI and sample LI 264. This is determined by summing the light intensities between the wavelength mask limits and dividing by the range of each wavelength mask. The wavelength mask is the range of wavelengths used to determined light intensity values from the acquired spectrum. FIG. 9 shows a spectral output of a recombined light from the optical path, the area below the cut-off wavelength 258 is between 525 and 537.5 nanometers and the area above the cut-off wavelength 260 is between 562.5 and 575 nanometers.

The third step is to calculate current sample ratio ($SR_{current}$) 266. This is done by dividing LI (area above cut-off wavelength 260) for different known concentrations of material in a liquid from measurement chamber by the base LI (area below the cut-off wavelength 258) from the primary optical path (see FIG. 10).

$$SR_{current} = \frac{\text{Sample Light Intensity}}{\text{Base Light Intensity}}$$

In the next step, $SR_{OPPM}$ is determined by dividing the sample LI (area above cut-off wavelength 260) for the blank sample from the measurement chamber 200 by the base LI (area below the cut-off wavelength 258) from the primary optical path.

$$SR_{OPPM} = \frac{\text{Sample Light Intensity}}{\text{Base Light Intensity}}$$

This step is known as store current sample ratio as zero PPM ratio 268.

The light control module 226 determines the $SR_{OPPM}$, and is stored after which further blank sample readings can be taken and compared against the blank sample $SR_{OPPM}$. If $SR_{OPPM}$ is determined, the value stored in these steps can be skipped throughout the remainder of the standard operation. Otherwise, a determination is made of "Is zero PPM sample ratio ($SR_{OPPM}$) set" 270? If "no," the cycle is repeated until a current sample ratio at zero PPM ratio 268 is determined.

If the $SR_{OPPM}$ is set, then calculate absorption 272 will occur by dividing $SR_{OPPM}$ by $SR_{current}$, which is generated for different known concentrations of material in a liquid.

$$\text{Absorbance} = \text{Log}_{10}\left(\frac{SR_{OPPM}}{SR_{current}}\right)$$

If the output for the light source 216 drops by ten percent, both the base and sample light intensities can be expected to drop by ten percent. As absorption is based on the zero and current sample ratios, the respective ratios will remain constant, negating the effect of varying light output due to the LED fatigue of the light source 216, changes in environment, or changes in operating temperature.

The final step is to convert the absorption value (ABS) into a PPM value using a polynomial equation of order 3 by setting y-intercept to zero in the calculate PPM reading 274 step.

Reading=$a*ABS^3 + b*ABS^2 + c*ABS$,

The reading value should be zero if the absorption is zero; however, a constant value is not always used.

Illustrative examples of how the steps in the flow chart (FIG. 10) illustrating the operational logic of the light control module are used to determine readings, and illustrate how the system behaves under different conditions. Any reference to spectrum charts, light intensity counts, wavelengths or any other figures are for demonstrational purposes.

Example 1—Blank Sample

Figure 11A:
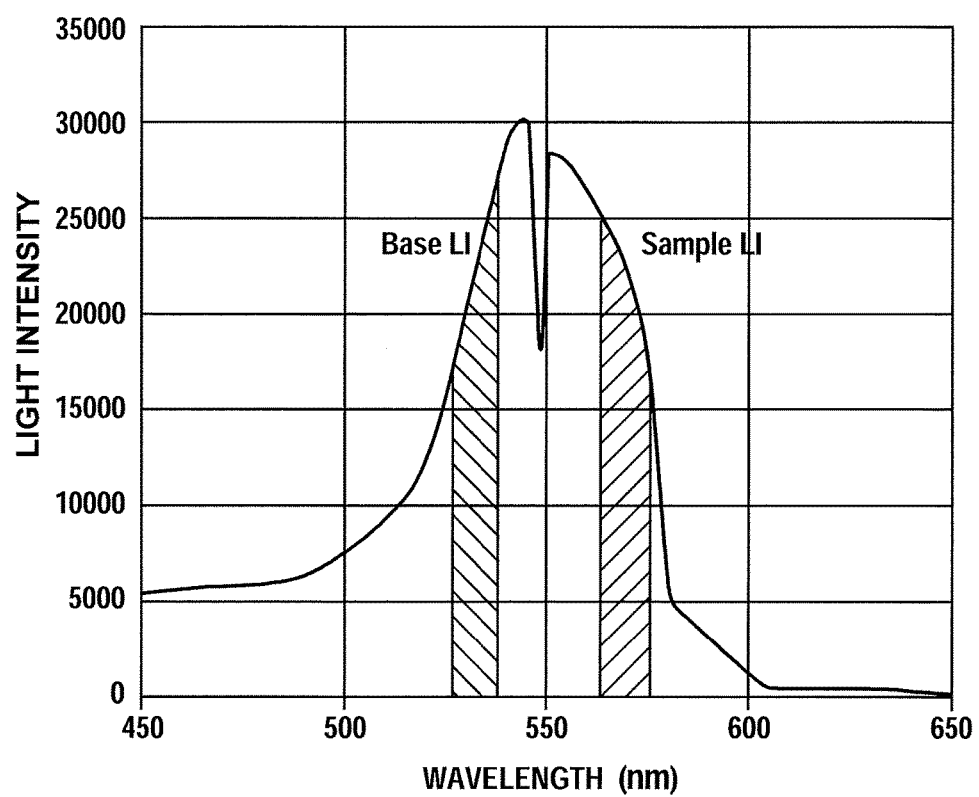
FIGS. 11A-11D are illustrative diagrams comparing light intensity to wavelength with various samples.

The first example (Blank Sample), assumes that the system is measuring a blank sample, and the $SR_{OPPM}$ value has been set at 1.0633.
1. Spectrum is acquired
2. Base and sample masks are calculated:
   Base LI: 21,000
   Sample LI: 19,750
3. Current Sample ratio is calculated:
   19750/21000=0.9405
4. Absorbance is calculated:
   $\text{Log}_{10}$(0.9405/0.9405)=0.00 absorbance
See FIG. 11A.

Example 2—Oil in Chamber

Figure 11B:
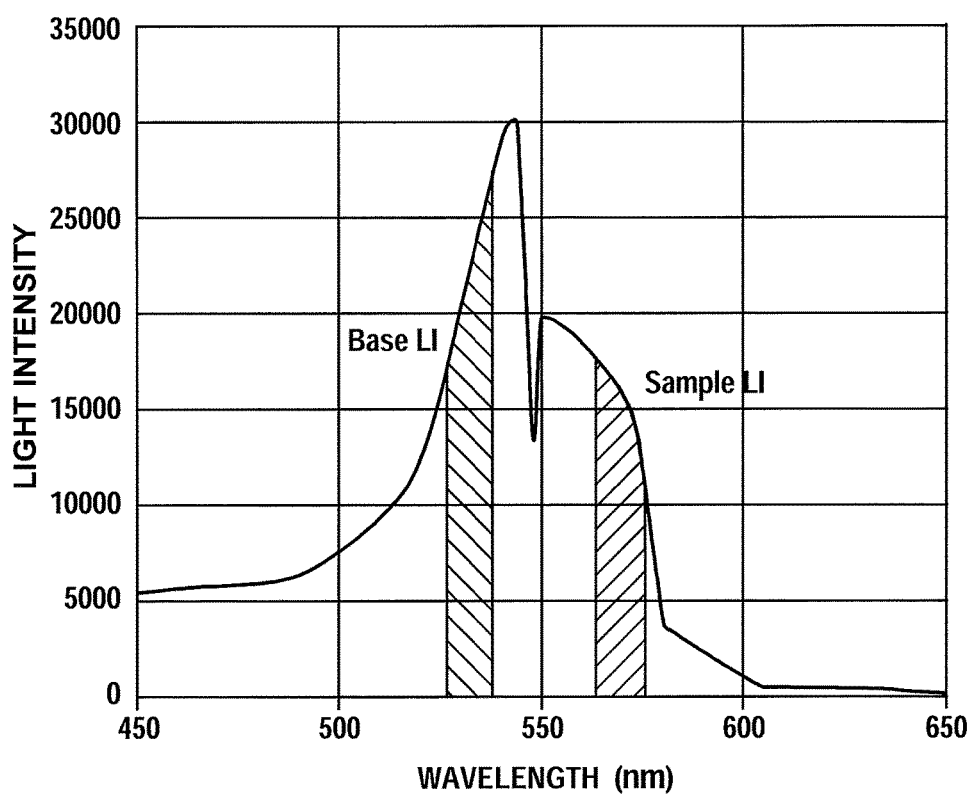

The second example (Oil in Chamber) assumes that oil is placed into the measuring chamber, and that it absorbs a portion of the light intensity on the sample path. The chart below shows that the overall spectral intensity for the sample leg is reduced. Calculating the absorbance assuming that the $SR_{OPPM}$ is still 1.0633 as mentioned in Example 1.
1. Spectrum is acquired
2. Base and sample masks are calculated:
   Base LI: 21,000
   Sample LI: 14,000
3. Current Sample ratio is calculated:
   14000/21000=0.6667
4. Absorbance is calculated:
   $Log_{10}$(0.9405/0.6667)=0.1494 absorbance See FIG. 11B.

Example 3—Degraded Light

Example 3 assumes that the same oil sample is present as for Example 2. However, the light output has decreased by ten percent.
1. Spectrum is acquired
2. Base and sample masks are calculated:
   Base LI: 18,900
   Sample LI: 12,600
3. Current Sample ratio is calculated:
   12600/18900=0.6667
4. Absorbance is calculated:
   $Log_{10}$(0.9405/0.6667)=0.1494 absorbance—identical to the reading in example 2

Figure 11C:
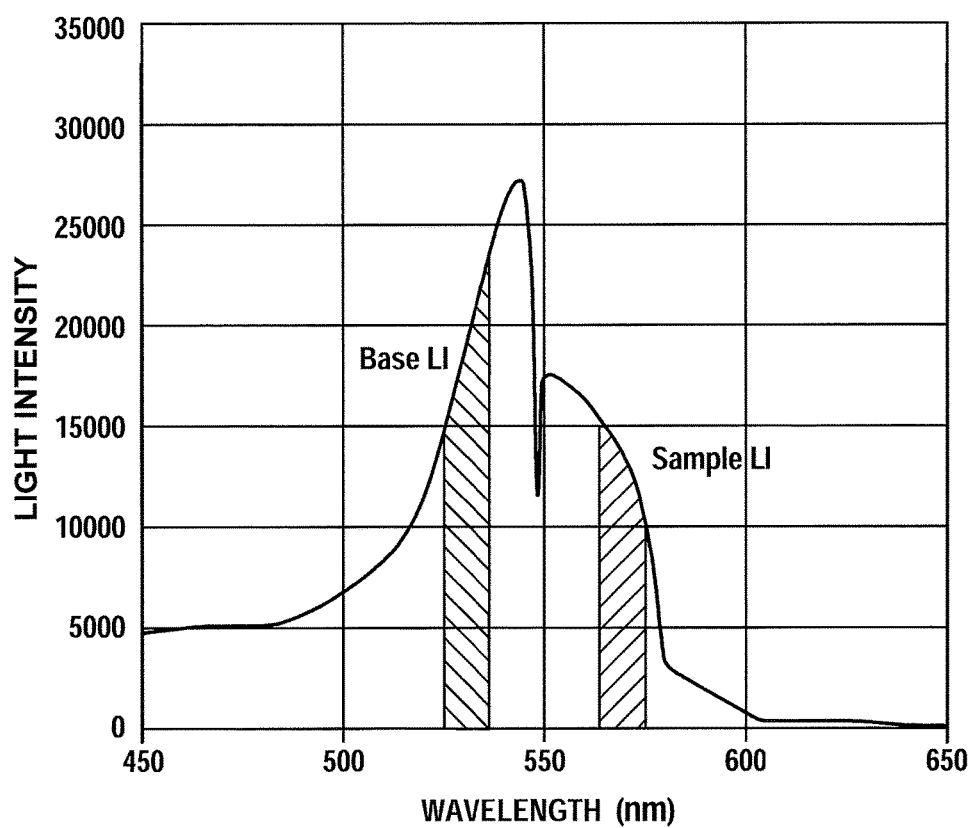

See FIG. 11C.

Example 4—Blank Sample

Example 4 assumes that the measuring chamber contains a blank sample, similar to Example 1, with the light source remaining degraded.
1. Spectrum is acquired
2. Base and sample masks are calculated:
   Base LI: 18,900
   Sample LI: 17,775
3. Current Sample ratio is calculated:
   17775/18900=0.9405
4. Absorbance is calculated:
   $Log_{10}$(0.9405/0.9405)=0.000 absorbance—identical to the reading in example 1

Figure 11D:
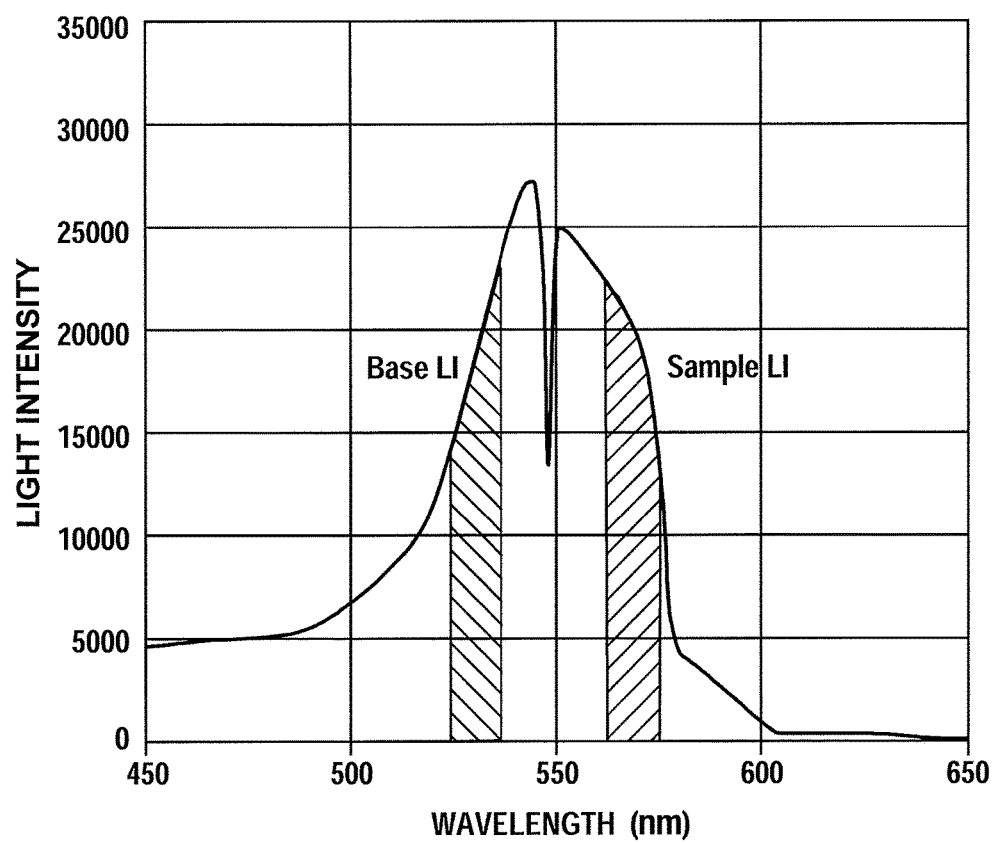

See FIG. 11D.

Figure 7:
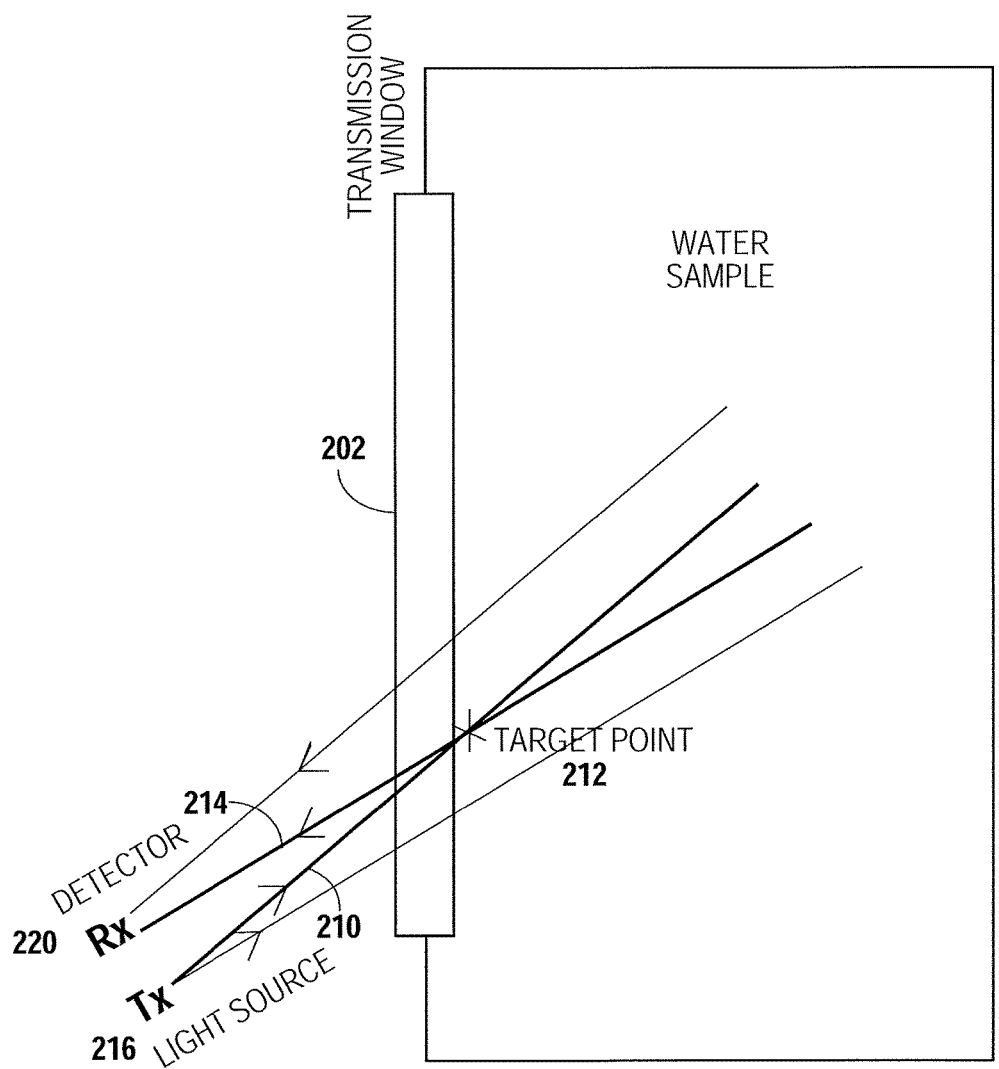
FIG. 7 is a pictorial view of a measurement chamber to be used with the apparatus shown in FIG. 6.

FIG. 7 is a schematic view of measurements made at the target point 212, which is just inside of the measurement window 202. The transmitted signal 210 travels to the target point 212 and the absorbed light 214 is what is furnished to the detector 220. Light source 216 is what provides the transmitted signal 210.

We claim:

1. An apparatus for measuring of material in a liquid through the absorption of light, the apparatus comprising:
   a measurement chamber with a measurement window through which a transmitted signal projects to a target point and an absorbed light signal is reflected from the target point in response to at least a portion of the transmitted signal being absorbed by the material in the liquid,
   a coupling mass with piezoelectric transducers being connected to said measurement window to cause vibrations of the measurement window to keep said measurement window clean;
   a source of power for said apparatus;
   a blank sample for calibrating said apparatus;
   a light source for generating said transmitted signal;
   a first beam splitter, wherein the first beam splitter is reflective below a cut-off wavelength and transmissive above the cut-off wavelength, wherein the first beam splitter receives light from the light source, wherein the light is split by the first beam splitter so that a first portion of the light with first wavelengths above the cut-off wavelength is projected to said target point as the transmitted signal, and wherein a second portion of the light with second wavelengths below the cut-off wavelength is reflected to a second beam splitter as a reflected light signal;
   the second beam splitter to receive said absorbed light signal from said target point and said reflected light signal from said first beam splitter and output recombined light beams, said second beam splitter being reflective above the cut-off wavelength and transmissive below the cut-off wavelength;
   a detector for receiving said recombined light beams; and
   a light control module connected to said light source and said detector, said light control module compensating for deviations in intensity of said transmitted signal by:
   calibrating with said blank sample, and
   calculating absorption based on the following:

$$Absorbance = Log_{10}\left(\frac{SR_{OPPM}}{SR_{current}}\right),$$

where $SR_{current}$ is a current sample ratio and is calculated by dividing a measured light intensity above the cut-off wavelength by a measured light intensity below the cut-off wavelength for the current sample, and wherein $SR_{OPPM}$ is determined by dividing light intensity above the cut-off wavelength by light intensity below the cut-off wavelength for the blank sample.

2. The apparatus of claim 1, further comprising at least one collimator for said first beam splitter and said second beam splitter.

3. The apparatus of claim 2, wherein said calibrating includes dividing the measured light intensity above said cut-off wavelength by the measured light intensity below said cut-off wavelength for the current sample to give said current sample ratio $SR_{current}$.

4. The apparatus of claim 3, wherein said calculating includes storing zero parts per million (PPM) for said blank sample.

5. The apparatus of claim 4, wherein calculating the absorption includes converting absorbance (ABS) into parts per million (PPM) by an equation and setting y-intercept to zero as follows:

$$Reading=a*ABS^3+b*ABS^2+c*ABS,$$

wherein Reading is a PPM concentration and a, b, and c are fitting parameters.

6. A method of determining material in a liquid through absorption of light comprising:
   flowing said liquid through a measurement chamber that includes a measurement window;
   generating a light beam;
   directing said light beam through a first beam splitter, wherein the first beam splitter is reflective below a cut-off wavelength and transmissive above the cut-off wavelength, wherein the first beam splitter splits the light beam so that a first portion of the light beam with wavelengths above the cut-off wavelength form a transmitted signal, and wherein a second portion of the light beam with wavelengths below the cut-off wavelength form a first reflected signal;

directing said transmitted signal through a single channel and said measurement window to a target point adjacent the measurement window;

receiving, at a second beam splitter, an absorbed light signal from said target point through said single channel, wherein the absorbed light signal is reflected from the target point in response to a portion of the transmitted light being absorbed by the material, wherein the second beam splitter is reflective above said cut-off wavelength and transmissive below said cut-off wavelength, and wherein the second beam splitter forms a recombined light beam output comprising said first reflected signal from the first beam splitter and said absorbed light signal;

detecting said recombined light beam output by a detector;

calibrating by putting a blank sample in said measurement chamber and calculating a current sample ratio ($SR_{current}$) and storing the current sample ratio as zero parts per million (PPM), wherein $SR_{current}$ is calculated by dividing a measured light intensity above the cut-off wavelength by a measured light intensity below the cut-off wavelength for the current sample;

determining ($SR_{OPPM}$) by dividing light intensity above said cut-off wavelength by light intensity below said cut-off wavelength for the blank sample; and calculating absorption using the equation $$\text{Absorbance} = \text{Log}_{10}\left(\frac{SR_{OPPM}}{SR_{current}}\right).$$

7. The method of claim 6, further comprising:

converting absorbance (ABS) into PPM by an equation and setting Y intercept to zero as follows:

Reading=$a$*ABS$^3$+$b$*ABS$^2$+$c$*ABS, wherein Reading is a PPM concentration and a, b, and c are fitting parameters.

* * * * *

UNITED STATES PATENT AND TRADEMARK OFFICE
CERTIFICATE OF CORRECTION

PATENT NO. : 10,197,545 B2
APPLICATION NO. : 15/340536
DATED : February 5, 2019
INVENTOR(S) : Jeyan Sreekumar et al.

It is certified that error appears in the above-identified patent and that said Letters Patent is hereby corrected as shown below:

On the Title Page

Please correct the Applicant to:
(71) Applicant: Advanced Sensors Limited,

Signed and Sealed this
Sixteenth Day of April, 2019

Andrei Iancu
*Director of the United States Patent and Trademark Office*